US009587251B2

(12) United States Patent
Ohta et al.

(10) Patent No.: US 9,587,251 B2
(45) Date of Patent: Mar. 7, 2017

(54) METHOD OF INDUCING HOMOLOGOUS RECOMBINATION OF SOMATIC CELL

(75) Inventors: Kunihiro Ohta, Saitama (JP); Hidetaka Seo, Saitama (JP); Takehiko Shibata, Saitama (JP)

(73) Assignees: Riken, Saitama (JP); Chiome Bioscience, Inc., Tokyo (JP)

( * ) Notice: Subject to any disclaimer, the term of this patent is extended or adjusted under 35 U.S.C. 154(b) by 0 days.

(21) Appl. No.: 10/540,302

(22) PCT Filed: Dec. 22, 2003

(86) PCT No.: PCT/JP03/16496
§ 371 (c)(1),
(2), (4) Date: Sep. 14, 2005

(87) PCT Pub. No.: WO2004/058964
PCT Pub. Date: Jul. 15, 2004

(65) Prior Publication Data
US 2006/0099678 A1    May 11, 2006

(30) Foreign Application Priority Data
Dec. 26, 2002  (JP) ................................. 2002-376555

(51) Int. Cl.
C12N 15/90        (2006.01)
(52) U.S. Cl.
CPC .................................. *C12N 15/902* (2013.01)
(58) Field of Classification Search
None
See application file for complete search history.

(56) References Cited

PUBLICATIONS

Yamazoe et al., DNA repair 3:1175-1185 (2004).*
Yang et al. J. Exp. Med. 203, 13:2919-2928 (2006).*
Winding et al. J. Immunol. Methods 249:1-16 (2001).*
PCT Notification of Transmittal of Translation of the International Preliminary Report on Patentability, dated Aug. 25, 2005 for application PCT/JP2003/016496, filed Dec. 22, 2003.
Nickoloff, J.A., "Transcription Enhances Intra chromosomal Homologus Recombination in Mammalian Cells", Mol. Cell. Biol., (1992), vol. 12, No. 12, pp. 5311-5318, full text.
Buerstedde, J. and Takeda, S., "Increased Ratio of Targeted to Random Integration after Transfection of Chicken B. Cell Lines", Cell., (1991), vol. 67, No. 1, pp. 179-188, full text.
Chen, J., et al., "Mutations of the intronic IgH enhancer and its flanking sequences differentially affect accessibility of the JH locus", EMBO. J., (1993), vol. 12, No. 12, pp. 4635 to 4645, full text.
Forrester, W.C., et al., "Dependence of Enhancer-Mediated Transcription of Immunoglobulin μ Gene on Nuclear Matrix Attachment Regions", Science, (1994), vol. 265, pp. 1221-1225, full text.
Bachl, J. and Wabl, M., "Enhancers of hypermutation", Immunogenetics, (1996), vol. 45, No. 1, pp. 59-64, full text.

Betz, A.G. et al., "Element Regulating Somatic Hypermutation of an Immunoglobulin κ Gene: Critizal Role for the Intron Enhancer/Matrix Attachment Region", Cell, (1994), vol. 77, No. 2, pp. 239-248, full text.
Bachl, J. and Wabl, M., "An Immunoglobulin mutator targets G•C base pairs", Proc. Natl. Acad. Sci. USA, (1996), vol. 93, pp. 851-855, full text.
Lahti, J.M., "Use of Gene Knockouts in Cultured Cells to Study Apoptosis", Methods, (1999), vol. 17, No. 4, pp. 305-312, full text.
Slebos, R. and Taylor, J.A., "A Novel Host Cell Reactivation Assay to Assess Homologous recombination Capacity in Human Cancer Cell Lines", Biochemical and Biophysical Research Communications, (2001), vol. 281, No. 1, pp. 212-219, full text.
Arakawa, H., et al., "Requirement of the Activation-Induced Deaminase (AID) gene for Immunoglobulin Gene Conversion", Science, (2002), vol. 295, pp. 1301-1306, full text.
Phi-Van, L. and Stratling, W.H., "Dissection of the Ability of the Chicken Lysozyme Gene 5' Matrix Attachment Region to Stimulate Transgene Expression and to Dampen Position Effects", Biochemistry (1996), vol. 35, No. 33, pp. 10735-10742.
Bulfone-Paus, S., et al., "The Chicken Immunoglobulin λ light chain gene is transcriptionally controlled by a modularly organized enhancer and an octamer-dependent silencer", Nucleic Acids Research, (1995), vol. 23, No. 11, pp. 1997-2005.
Lauster, R., "Promoter, enhancer and silencer elements regulate rearrangement of an immunoglobulin transgene", The EMBO Journal, (1993), vol. 12, No. 12, pp. 4615-4623.
Israel, D. and Kaufman, R., "Highly inducible expression from vectors containing multiple GRE's in CHO cells overexperssing the glucocorticoid receptor" Nucleic Acids Research (1989), vol. 17, No. 12, pp. 4589-4604.
Chauhan, Shyam S., et al, Costruction of a new universal vector for insertional mutagenesis by homologous recombination, Gene, Elsevier, Amsterdam, NL, vol. 120, 1992, pp. 281-285, XP002911851, ISSN: 0378-1119.
Kanayama et al., "Genetic manipulation of an exogenous non-immunoglobulin protein by gene conversion machinery in a chicken B cell line," Nucleic Acids Research, 34(2): 1-9 (2006).
Reynaud et al., "A Hyperconversion Mechanism Generates the Chicken Light Chain Preimmune Repertoire," Cell, 48: 379-388 (Feb. 13, 1987).
van Gent et al., "The RAG1 and RAG2 Proteins Establish the 12/23 Rule in V(D)J Recombination," Cell, 85: 107-113 (Apr. 5, 1996).
Arakawa and Buerstedde, "Immunoglobulin Gene Conversion: Insights From Bursal B Cells and the DT40 Cell Line," Developmental Dynamics, 229: 458-464 (2004).
Thompson, C.B. et al.; "Somatic Diversification of the Chicken Immunoglobulin Light Chain Gene is Limited to the Rearranged Variable Gene Segment"; Cell, 48: 369-378 (Feb. 13, 1987) (10 pgs.).
Kim, S. et al.; "Ongoing Diversification of the Rearranged Immunoglobulin Light Chain Gene in a Bursal Lymphoma Cell Line"; Mol. Cell. Biol., 10(6): 3224-3231 (Jun. 1990) (8 pgs.).
Buerstedde, J.-M. et al.; "Light chain gene conversion continues at high rate in an ALV-induced cell line"; EMBO J., 9(3): 921-927 (1990) (7 pgs.).
Seo, H. et al.; "Rapid generation of specific antibodies by enhanced homologous recombination"; Nat. Biotech., 23(6): 731-735 (Jun. 2005) (5 pgs.).
Nickoloff et al., "Transcription Stimulates Homologous Recombination in Mammalian Cells," Mol. Cell. Biol., 10(9): 4837-4845 (1990).

* cited by examiner

Primary Examiner — Nancy Treptow
(74) Attorney, Agent, or Firm — Finnegan, Henderson, Farabow, Garrett & Dunner, LLP

(57)    ABSTRACT

The present invention provides a method for obtaining diverse novel genes by inducing somatic cell homologous recombination at genetic loci in somatic cells.

(Continued)

By controlling transcription activity of a gene that exists at a genetic locus in a eukaryotic organism cell wherein DNA homologous recombination is occurring at an arbitrary genetic locus, somatic cell homologous recombination is induced between said gene and a gene having a DNA sequence similar to said gene that exists in a region upstream of a transcription promoter, whereby it is possible to obtain diverse novel genes having a plurality of genetic information.

15 Claims, 5 Drawing Sheets

Fig. 2

Fig. 3 conversion rate = F/E(%)

METHOD OF INDUCING HOMOLOGOUS RECOMBINATION OF SOMATIC CELL

TECHNICAL AREA

The present invention generally relates to an art for inducing somatic cell homologous recombination in a cell of a eukaryotic organism, and more specifically concerns a method for inducing somatic cell homologous recombination at an arbitrary genetic locus in a somatic cell, and a cell wherein somatic cell homologous recombination is induced by said method.

Additionally, the present invention also concerns a method for producing a novel gene having a plurality of genetic information, by using the aforementioned somatic cell homologous recombination induction method.

Further, the present invention concerns a novel protein encoded by the abovementioned novel gene.

Still further, the present invention concerns a vector used for, and having been constructed in a structure optimal for, inducing somatic cell homologous recombination.

BACKGROUND ART

For eukaryotic organisms, the homologous recombination of somatic cells is one of the most important DNA metabolic reactions for obtaining a diversity of genes, and as a result, for producing diverse protein activity. Therefore, the control of homologous recombination of somatic cells is one of the extremely important problems for obtaining a diversity of genes.

Conventionally, as a method for obtaining a diversity of genes having new functions or attributes, there is the art of DNA shuffling (see, e.g., Crameri et al., 1998). This art simulates homologous recombination by mixing a plurality of homologous genetic sequences, appropriately digesting with DNaseI and using the resulting small fragments as primer, and conducting PCR with the original gene as a template. However, the analysis of recombination products is generally done after amplified fragments are linked to expression vectors, and transformed into bacteria, and it is thought that the direct analysis of what characteristics the products would have in higher eukaryotic organisms would be difficult. Additionally, checking expression within an animal cell requires that expression compatibility due to transfer into a new vector and codon usage be confirmed successively.

On the other hand, as systems that induce genetic recombination within animal cells, there are systems that activate recombination within cells, such as systems using the site specific recombination enzyme Cre-lox (see, e.g., DiSant et al., 1995), and systems using the sequence specific endonuclease I-SceI (see, e.g., Rouet et al., 1994). The Cre-lox system uses Cre, a 38 kDa site specific recombinase obtained from the bacteriophage P1, and inducts recombination between specific sites called loxP sites. Additionally, the I-SceI system utilizes the activity of I-SceI, an endonuclease derived from budding yeast, of cleaving a DNA double strand at a recognition site thereof, and inducing DNA homologous recombination. However, in these systems, because recombination is restricted to being between specific sequences, and the recombination event is one-shot, the recombinants that could be obtained were in principle only one type. Additionally, since it was necessary to introduce a sequence relating to the control of the recombination into a chromosome beforehand to cause recombination enzymes such as Cre or I-SceI to be expressed within a cell, the induction of recombination of chromosomes was not easy.

DISCLOSURE OF THE INVENTION

The inventors of the present invention, having considered the abovementioned state of affairs, conducted penetrating research into whether or not a method exists for inducing somatic cell homologous recombination under controlled conditions, and as a result, found to their surprise that by controlling transcription at genetic loci where recombination is desired, it is possible to induce somatic cell homologous recombination between similar base sequences.

Accordingly, in general, the present invention has the objective of providing a method for inducing somatic cell homologous recombination at a genetic locus in a somatic cell.

Additionally, the present invention has the objective of providing a cell wherein somatic cell homologous recombination is induced by the abovementioned method.

Further, the present invention has the objective of providing a novel gene having a plurality of genetic information and a method for producing said novel gene, by using somatic cell homologous recombination induced within a cell.

Still further, the present invention has the objective of providing a novel protein encoded by said novel gene.

Additionally, the present invention has the objective of providing a vector with a structure constructed in order to desirably control transcription and to be used to induce somatic cell homologous recombination.

Further, the present invention provides an induction method for somatic cell homologous recombination characterized by somatic cell homologous recombination of a eukaryotic organism cell wherein DNA homologous recombination can occur at an arbitrary genetic locus, whereby, by controlling the transcription of a gene at said genetic locus, DNA homologous recombination is induced between said gene and a similar base sequence. Additionally, a cell is also provided wherein somatic cell homologous recombination is induced by said method.

Additionally, the present invention provides a method for obtaining a novel gene having a plurality of genetic information, by somatic cell homologous recombination of a eukaryotic organism cell wherein DNA homologous recombination can occur at an arbitrary genetic locus, whereby, by controlling the transcription of a gene at said genetic locus, DNA homologous recombination is induced between said gene and a similar base sequence. Additionally, a novel gene produced by said method is also provided.

Still further, a novel protein encoded by said novel gene is also provided.

Additionally, the present invention provides a constructed vector with the structure necessary to desirably control transcription, used in order to induce somatic cell homologous recombination.

By using the art disclosed in the specification of the present invention, since DNA homologous recombination is induced continuously at various locations, it is possible to increase diversity of the obtained recombinants. Additionally, by using the art disclosed in the present specification, since the objective genes having genetic diversity are spontaneously formed within objective cells, without producing a DNA library for recombination required for DNA shuffling technology, screening can be done within said cells for the production of the desired novel gene. Therefore, a diversity of novel genes is obtainable in a time shorter than for the conventional art.

For the eukaryotic organism cells that may be used for the present invention, it is thought that any cell wherein somatic cell homologous recombination may occur at an arbitrary genetic locus is usable, but preferably, chicken derived DT40 cultured cells should be used.

A gene for which somatic cell homologous recombination is induced may be an endogenous gene or an exogenous gene. Additionally, among base sequences similar to said gene are included, for example, genetic sequences that exist in nature, base sequences that exist in nature which do not have the form of a gene, and man-made sequences.

In the case of an endogenous gene, it is utilizable if it exists at a genetic locus where a sequence similar to said gene exists upstream and in the vicinity of a transcription promoter that promotes the transcription activity of said gene, and for example, antibody light chain or heavy chain gene loci are utilizable.

Additionally, in the case of an exogenous gene, any gene is utilizable, as long as it is constructed on an appropriate vector with a structure including a transcription promoter upstream of a gene that produces homologous recombination, and a sequence in the vicinity and further upstream similar to said gene.

Here, it is sufficient for the base sequences similar to the objective gene to be located in the region approximately 1 bps to 100 kbps upstream from the transcription initiation location of the objective gene, but this should more preferably be located in a region approximately 500 bps to 50 kbps upstream, and even more preferably approximately 3 kbps to 25 kbps upstream.

As an exogenous gene, there are no restrictions, but fluorescent protein genes (e.g., GFP genes, CFP genes and the like), drug resistance genes (e.g., hygromycin resistance gene, or puromycin resistance gene) and the like are included.

The "base sequence similar to a gene for which somatic cell homologous recombination is induced" used in the present invention is a base sequence that is similar to the entirety or one portion of said gene. Here, similar means having 60% or greater sequence identity, preferably 70% or greater sequence identity, and more preferably 80% to 99%, including 80%, 82%, 82%, 83%, 84%, 85%, 86%, 87%, 88%, 89%, 90%, 91%, 92%, 93%, 94%, 95%, 96%, 97%, and 99% sequence identity with the entirety or one portion of a gene for which somatic cell homologous recombination is induced.

For the transcription control method used in the present invention, any method well-known to those skilled in the art is usable, but a method using an endogenous transcription promoter, or a method of control using an endogenous inducible transcription promoter is preferable.

Additionally, in order to promote transcription activity, an enhancer and a nuclear matrix attachment region (MAR) appropriate for the objective gene may be used. In order to control transcription, it is necessary to align the transcription promoter, the enhancer, and the nuclear matrix attachment region (MAR) in an action-capable manner. Here, "action-capable" means that the transcription promoter, enhancer, and nuclear matrix attachment region (MAR) can realize each of their functions, and that the transcription of the objective gene is controlled as desired. For example, in the case of a transcription promoter, there are no particular restrictions, but it should be located in a region within approximately 100 bps upstream of the transcription initiation location of the objective gene, and in the case of the enhancer, there are no restrictions, but normally, it may exist 100 bps or more, or several thousand bps or more from the transcription initiation point, and may be on the 5' side or the 3' side of the objective gene. Additionally, the nuclear matrix attachment region (MAR) is located adjacent to the enhancer, and may be on the 3' side or the 5' side of the enhancer.

BEST MODES FOR EMBODYING THE INVENTION

Since the method of homologous recombination of the Enhanced Cyan Fluorescent Protein (ECFP) gene utilizes in part the induction method for somatic cell homologous recombination according to the present invention, herebelow, the method of homologous recombination of the enhanced cyan fluorescent protein (ECFP) gene shall be explained in detail.

As mentioned above, in the homologous recombination method for enhanced cyan fluorescent protein (ECFP) genes of the present invention, cells wherein DNA homologous recombination is occurring are selected and cultivated, and when inducing homologous recombination, DNA homologous recombination of said cells is regulated by an inducible promoter, to induce homologous recombination with enhanced green fluorescent protein (EGFP) gene sequences having a base sequence similar to ECFP.

Therefore, herebelow, selection and cultivation of cells, construction of a vector for induced transcription control, confirmation of expression of a novel gene wherein homologous recombination is induced, and confirmation of a novel gene sequence wherein homologous recombination is induced shall be explained in order.

1. Selection of Cells Wherein Somatic Cell Homologous Recombination is Induced

"Eukaryotic cells" in the present invention refer to cells wherein somatic cell homologous recombination occurs with some frequency, preferably being human, mouse, sheep, rat, rabbit, or chicken B cells or cell lines thereof, more preferably being human Burkitt's lymphoma derived Ramos cell lines, or chicken B cell derived DT40 cell lines, and most preferably being DT40 cell lines.

The "DT40 cell lines" used in the present invention include derived cell lines and sublines wherein the chromosomes of said cells have been modified in some manner (e.g., recombination, insertion, deletion, and the like of a specific gene).

The cultivation conditions used for the present invention are conducted in a manner publicly known in said technical field, but needless to say, this shall be performed in a medium and cultivation conditions (cultivation temperature, $CO_2$ concentration) appropriate for the selected cells. As a medium, the generally used RPMI1640 medium or DMEM medium, or media wherein fetal bovine serum has been added to these media, and the like, may be given as examples. Cultivation is normally done in the presence of 5% $CO_2$, for 1 to 30 days at the appropriate temperature (e.g., 25 degrees Celsius to 40 degrees Celsius) for the utilized cells. During cultivation, antibiotics such as kanamycin and penicillin may be added to the medium as needed during cultivation. Additionally, in cases where transcription control is done using an inducible promoter, a drug for inducing the transcription may be added (e.g., tetracycline). Thus, in cases where the selected immune cells are DT40 cells, for example, IMDM (Invitrogen) is used as the medium, the cultivation temperature is, for example, 39.5 degrees Celsius, and cultivation is done in a 5% $CO_2$ concentration.

2. Construction of a Vector for Transcription Control (1) Cis-Acting Region

As the method for transcription control used in the present invention, any method may be used as long as it is a well-known art for those skilled in the art, but preferably a method is used wherein a cis-acting region for transcription control is constructed on an appropriate vector, and by introducing said vector into a cell, incorporating it into a specific genetic locus on the chromosome. Here, the "cis-acting region" refers to a DNA sequence necessary for the transcription control of a specific gene, being a region that exists adjacent to said gene. A "cis-acting region" includes transcription promoters, enhancers, nuclear matrix attachment regions (MAR), and other arbitrary sequences that are necessary for controlling transcription activity.

For the transcription promoter, either constitutive promoters or inducible promoters are usable, but from the fact that transcription control is easy, inducible promoters are preferable. Inducible promoters include promoters that respond to α-interferon, heat shock, heavy metal ions, steroids such as glucocorticoids (Kaufman, 1990), and tetracycline. Other desirable inducible promoters include those which respond within a cell when the activation factor for a promoter is added from the outside. Preferably, for example, a tetracycline inducible promoter or the like is usable.

Any enhancer and nuclear matrix attachment region (MAR) is usable, as long as they function for the control of transcription activity within selected cells, but in cases where DT40 cells are used, it is preferable to use a chicken antibody light chain gene enhancer (3' enhancer) and a chicken-derived nuclear matrix attachment region.

Among the components constituting a cis-acting region, in cases where the sequences of the inducible promoter, enhancer, and nuclear matrix attachment region (MAR) are publicly known, it is possible to produce a primer in order to amplify said sequence by the PCR method or the like based on this sequence, and to obtain them directly from appropriate cDNA libraries or genome libraries. It is preferable for the primer used here to be designed so that, for convenience when cloning, a restriction enzyme site that exists on the vector for cloning is added. The obtained enhancer and nuclear matrix attachment region (MAR) may be cloned using an appropriately added restriction enzyme site, on a vector whereon are constructed a gene for which homologous recombination is to be induced, and a DNA sequence similar to said gene, in the order of a promoter between said gene and a similar DNA sequence, a nuclear matrix attachment region (MAR), and an enhancer, in the 3' direction downstream from said gene, or in the opposite order.

Additionally, the target gene, base sequence similar to said gene, enhancer, nuclear matrix attachment region (MAR), and the like may be cloned onto commercially available vectors, for example, pTRE2hyg (Clontech) on which inducible promoters have been pre-cloned.

(2) Obtaining the Gene (ECFP)

The gene for which homologous recombination is to be induced may be an endogenous gene, but it may also be an isolated exogenous gene. Because of ease of transcription control, exogenous genes are preferable.

The genes for which homologous recombination is to be induced are cloned by methods well-known to those skilled in the art, but said genes may be amplified by using a primer set (e.g., a primer pair set designed so that said gene is amplifiable on the 5' end and the 3' end of said gene) usable for amplifying said gene, and a DNA polymerase with a highly accurate DNA polymerase (e.g., Pyrobest DNA Polymerase (TaKaRa)).

The obtained gene can be cloned into an appropriate cloning vector (e.g., pBlueScriptII, pUC19 and the like).

In cases where the gene for which homologous recombination is induced is an ECFP gene, cloning may be done with a commercially available vector (pECFP-C1).

By a similar method, a base sequence similar to the entirety or a portion of the ECFP gene is obtainable. Any sequence similar to the ECFP gene is usable, but, for example, the EGFP gene sequence and the like are preferable.

As mentioned above, the obtained ECFP gene and the sequence similar to the ECFP gene are inserted in an action-capable manner on a vector whereupon a "cis-acting region" is constructed, on the upstream side of the ECFP gene (that is, the 5' side), with a transcription promoter in between. The direction in which the similar DNA sequence is inserted may be in the ordinal direction or the opposite direction. The "ordinal direction" refers to the naturally existing direction if the objective DNA sequence occurs naturally, and in cases where the sequence is man-made, either direction may be selected to be the "ordinal direction."

3. Construction of a Transcription Factor Expression Vector

In order to induce the somatic cell homologous recombination of a gene, the expression of a transcription factor necessary for the promotion or suppression of transcription promoter activity is necessary. For example, in the case of a tetracycline induced promoter, a transcription factor (e.g., a VP16 transcription activation domain fused to a Tet repressor) that regulates transcription by binding to a tetracycline response region. Vectors for expressing these transcription factors may include, for example, promoters linked action-capably relative to the expression of said transcription factors (e.g., human cyto megalovirus immediate early promoter), and appropriate selective markers (e.g., a neomycin resistance marker, a hygromycin resistance marker, and the like).

Additionally, as vectors for controlling promoters, commercially available vectors, such as pTet-Off or pTet-On vector (Clontech) may be used.

4. Confirming Expression of a Novel Gene for which Homologous Recombination has been Induced (1) Induction of Homologous Recombination of a Selected Gene In order to induce homologous recombination of a selected gene (here, an ECFP gene), a factor that further regulates the activity of a transcription factor for a promoter action-capably linked to an ECFP gene is needed. Said factor is determined depending on the transcription promoter selected, and this can be selected by those skilled in the art without an excessive amount of experiments and the like. For example, in cases where the selected promoter is a tetracycline inducible promoter, tetracycline or doxycycline and the like are usable as said factor.

Additionally, it is necessary to introduce a vector for transcription control and a transcription factor expression vector into the selected cells. As a method for introducing the vectors into the cells, any method well-known to those skilled in the art may be used, but for example, the calcium phosphate method (Chen and Okayama, 1988), or the cationic lipid method (Elroy-Stein and Moss, 1990), the electroporation method (Neumann et al., 1982), and the like may be used.

After having introduced the aforementioned two types of vectors into the cells, the objective transcription promoter is activated by adding or removing the factor necessary for activation of the transcription promoter (e.g., tetracycline, doxycycline, and the like) to the medium. By doing so, homologous recombination of the selected gene is induced.

(2) Confirming Expression of a Novel Gene for which Homologous Recombination is Induced The expression of a novel gene that is created by the induction of homologous recombination may be confirmed by using methods well-known to those skilled in the art, according to the characteristics of the genetic products prior to the induction of recombination. For example, in cases where the selected gene has a specific drug resistance, by comparing, for cells prior to the induction of homologous recombination, and cells after induction, tolerable concentrations and the like of a specific drug, the expression of a novel gene can be predicted. Additionally, in the case of ECFP genes, the expression of a novel gene may be confirmed by changes in the wavelength of the fluorescent light emitted, and the like.

5. Sequence Analysis of a Novel Gene Induced by Homologous Recombination

The creation of a novel gene can further be confirmed by conducting sequence analysis on the novel gene for which homologous recombination was done, and by the actual occurrence of homologous recombination.

The genomic DNA of a cell whereon confirmation of homologous recombination is to be done is extracted by a known method, and the objective gene is amplified by the PCR method using specific DNA primers (e.g., in order to include the entire objective genetic region, design a primer in the forward direction in the vicinity of the 5' side of said gene, and design a primer in the reverse direction on the 3 side of said gene) usable for the amplification of the gene to be confirmed.

A commercially available DNA polymerase may be used for amplification, but it is preferable to use one that is highly accurate. The conditions for conducting amplification depend on the annealing temperature of the DNA primer used, and the properties of the DNA polymerase used, but for example, after reacting for 2 minutes at 98 degrees Celsius, 26 cycles of 30 seconds at 98 degrees Celsius, 30 seconds at 58 degrees Celsius, 1 minute at 72 degrees Celsius, and further reacting at 72 degrees Celsius for 5 minutes. The amplification products after reacting are separated by agarose gel electrophoresis, DNA bands containing the objective genes are cut out, and DNA is recovered, then incorporated into a vector for sequencing. The vector for sequencing may be any vector used in said technical area, but, for example, pCR2.1-TOPO (Invitrogen) may be used. The DNA sequence of a gene in the abovementioned prepared vector for sequencing can be determined according to an established method.

Herebelow, embodiments shall be described, but the present invention is not restricted to these.

EMBODIMENT 1

Construction of a Vector for Induced Transcription Control

Figure 1:
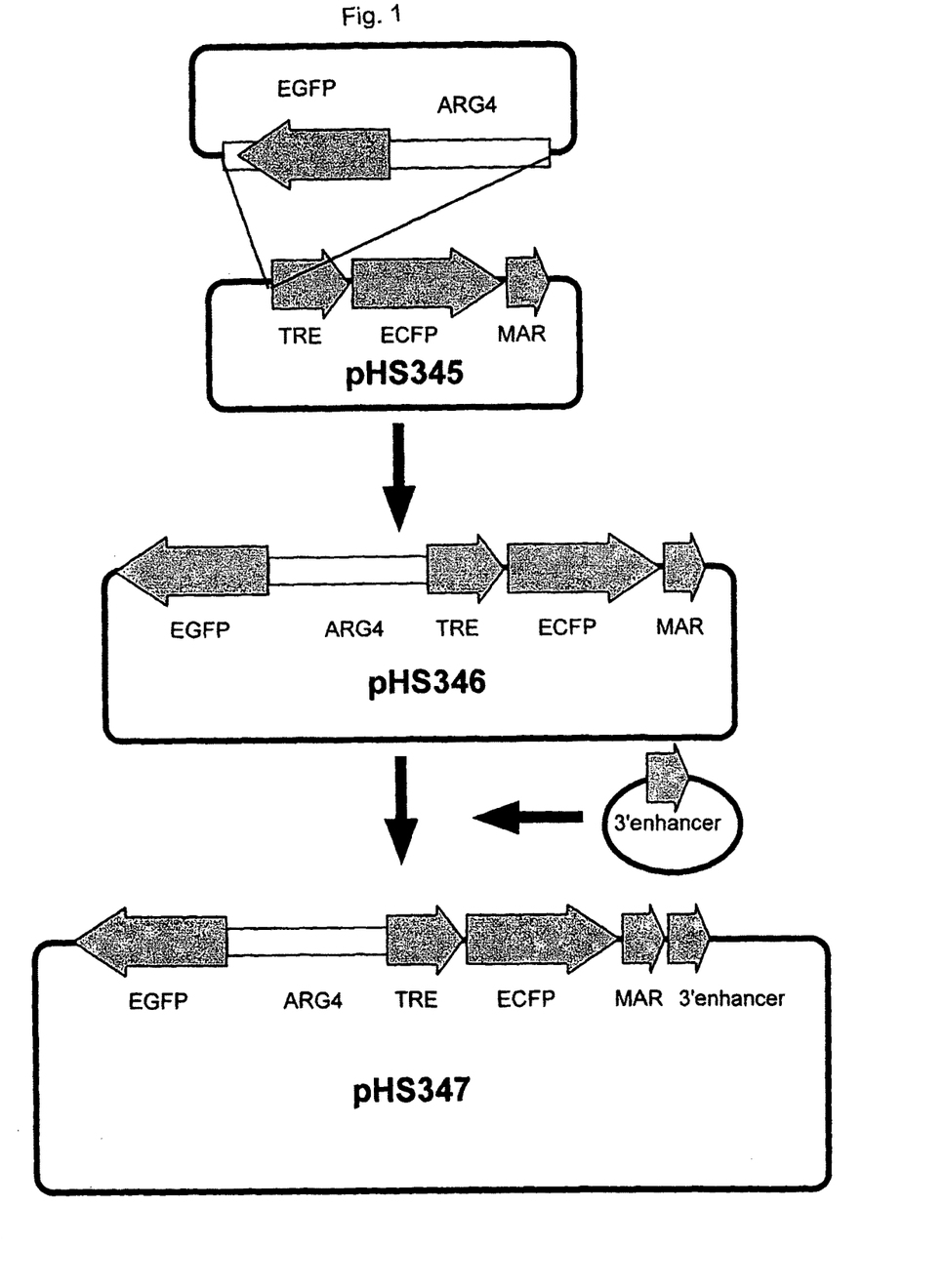
FIG. 1 shows an outline of a method for constructing on a vector a cis-acting region necessary for inducing transcription.

In order to introduce a promoter for inductively controlling the expression of a gene into a cell, a cis-acting region necessary for transcription induction was constructed on a vector (FIG. 1).

An ECFP gene was attached downstream of a tetracycline inducible promoter (TRE and human cyto-megalovirus mini-promoter) and a MAR and an enhancer (3' enhancer) were attached further downstream. Upstream, a spacer sequence of approximately 3 kb (Arg4 yeast gene, 3 kb PstI fragment) was placed, and further, EGFP was attached in the reverse direction to ECFP.

The PCR method was used for the cloning of the MAR and 3' enhancer. The Exp and High Fidelity PCR system, manufactured by Roche, was used for PCR, and this was conducted with a primer designed in the following way, using DT40 genomic DNA as a template.

MAR:

```
Forward direction primer
                                 (Sequence Number: 1)
5'-GCTGCAGTGTCCTTGGGGGTGAAATTCAG-3'

Reverse direction primer
                                 (Sequence Number: 2)
5'-GCTCTAGAACTGCCCCCATTAAAAACTTTC-3'
```

3' Enhancer:

```
Forward direction primer
                                 (Sequence Number: 3)
5'-GCTCTAGAAGGCACAGCGCTGTCAGGGTGC-3'

Reverse direction primer
                                 (Sequence Number: 4)
5'-CCGCGGCCGCGTGGTGGGAGCGGGCAGGGG-3'
```

After PCR products were once TA cloned to pCR2.1 vectors, and subsequently digested with an appropriate restriction enzyme (MAR: PstI, XbaI, 3' enhancer: XbaI, NotI), they were re-cloned into pBlueScriptII. For the tetracycline inducible promoter, an XhoI EcoRI fragment containing TRE, from pTRE2hyg (Clontech), was cloned into pBlueScriptII. The ECFP gene was inserted into this plasmid containing TRE. For the ECFP gene, NheI, MulI frangmentscontaining ECFP from pECFP-C1 plasmids (Clontech) were blunt-end ligated into pHS305 digested with EcoRI (pHS344). Further, MARs cloned into pBlueScriptII were inserted into a downstream portion of pHS344 ECFP (pHS345). As mentioned above, an ARG4 yeast gene was used as a spacer sequence. This is a 3 kb fragment created by the PstI attached to pUC119, but EGFP fragments (NheI, BspEI fragments of pEGFP-C1) were blunt-end ligated to SnaBI fragments of these plasmids. From here, sequences containing EGFP and ARG4 genes were cut out from PstI, and by blunt-end ligation of XhoI fragments of pHS345, pHS346 was obtained. Further, pHS347 was created by inserting 3' enhancer cloned into pBlueScriptII into pHS346 digested with XbaI and NotI.

EMBODIMENT 2

Preparation of Cells Wherein DNA Homologous Recombination is Induced (1) Cell Cultivation DT40 cells were cultivated in 5% $CO_2$ and 39.5 degrees Celsius in a $CO_2$ thermostatic oven. IMDM medium (Invitrogen) was used as the medium, with 10% FBS, 1% chicken serum, 100 units per ml of penicillin, 100 μg/ml of streptomycin, and 55 μM 2-mercapto ethanol added.

(2) Transfection

30 μg of an expression vector pTA-Hyg (clontech) expressing tetracycline inducible transcription factor was linearized with HindIII, and additionally, 60 μg of pHS347 was linearized with XmnI, and transfected into DT40 cells according to a known method (Buerstedde et al., 1991). At that time, 2.5 mg/ml hygromycin and 100 ng/ml doxycycline were added to the medium and selection was conducted. As a result among hygromycin resistant clones, clones which express ECFP in the absence of doxycycline were able to be obtained (HS101 cell line).

EMBODIMENT 3

Confirmation of Novel Gene Products

Figure 2:
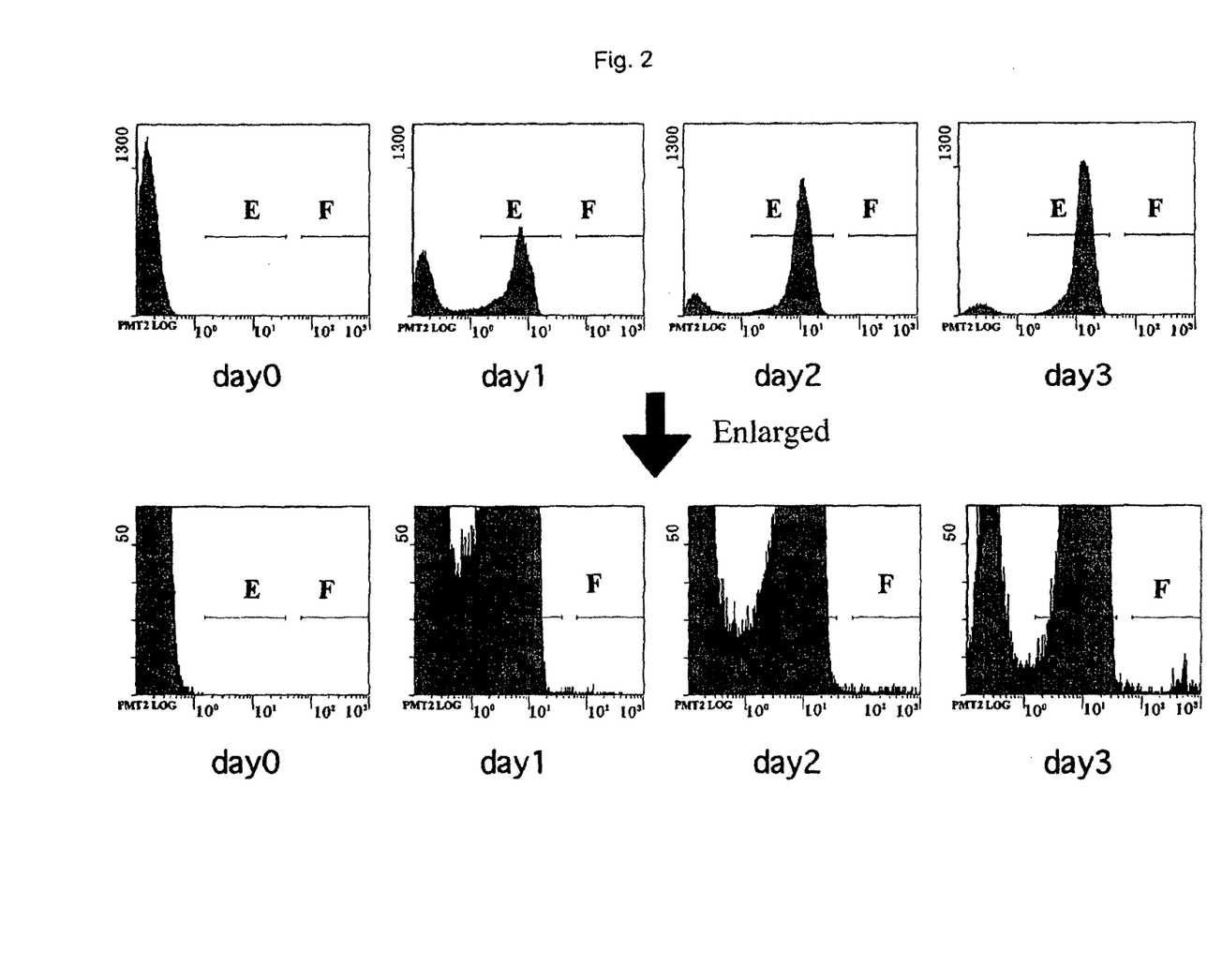
FIG. 2 shows the change over time of fluorescent intensity under FACS. Gate E is thought to be ECFP, and a group with even stronger fluorescent intensity was gated to F.
Figure 3:
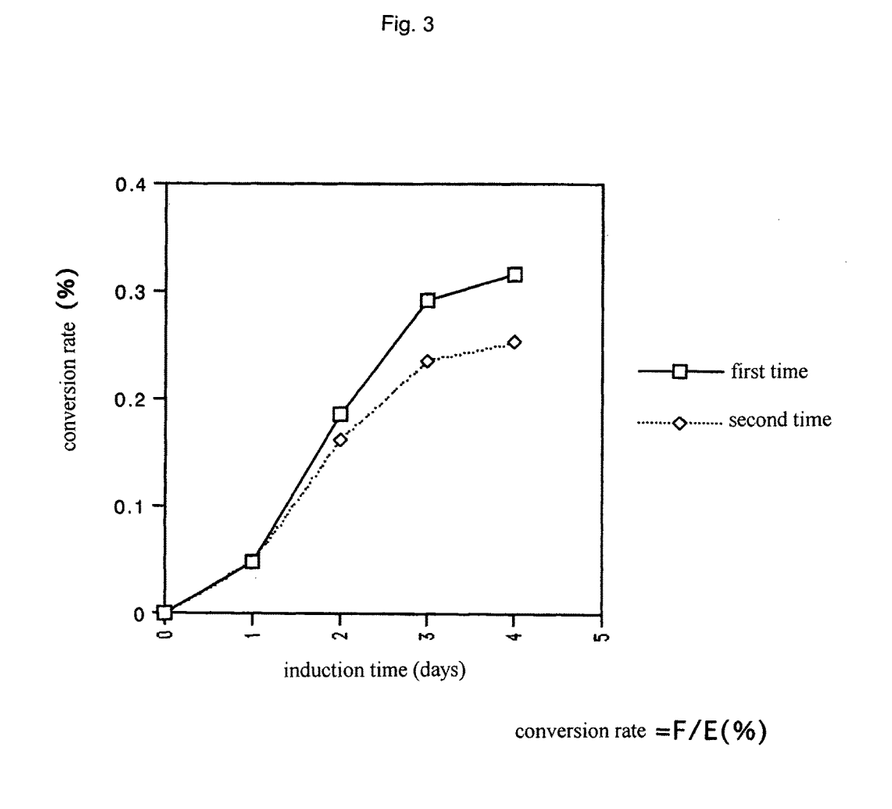
FIG. 3 shows the change over time of fluorescent intensity under FACS. Quantification was done by taking the ratio of the fluorescent intensity of E and the fluorescent intensity of F.
Figure 4:
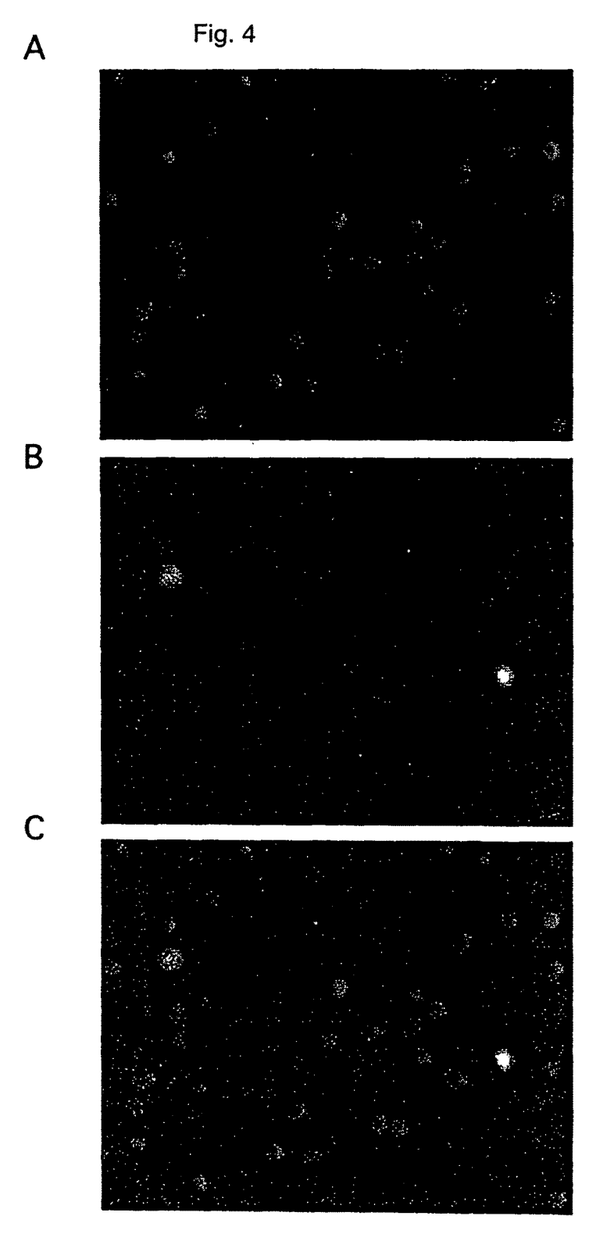
FIG. 4 shows an observed image of cells wherein homologous recombination was induced between the ECFP gene and the EGFP gene under a fluorescent microscope. This is a fluorescent microscope image 5 days after inducing transcription of ECFP. Among cells (A) wherein CFP fluoresces, cells (B) were observed (C) wherein GFP is thought to fluoresce.

HS101 was cultivated in the absence of doxycycline, and after measuring the fluorescent intensity with an EPICS ELITE ESP (manufactured by Beckman Coulter), a group emitting fluorescent light thought to be ECFP was observed (FIG. 2: gate E). When cultivation was continued, a group with an even stronger fluorescent intensity than ECFP was observed (FIG. 2: gate F). When the ratio of E to F was calculated, it was observed that the existence ratio of F increased depending on the cultivation time from the start of induction (FIG. 3). Further, when cells on the fifth day of cultivation after induction were observed with a fluorescent microscope, among cells emitting ECFP fluorescent light, cells emitting fluorescent light thought to be GFP were observed (FIG. 4).

EMBODIMENT 4

Analysis of Novel Genetic Sequence (1) Extraction of Genomic DNA

Cells in the vicinity of gate F in FACS were sorted, and 5000 cells were gathered in a silicone coated 1.5 ml tube, with an EPICS ELITE ESP (manufactured by Beckman Coulter). The cells suspended in the sheath fluid were recovered by centrifuge (1000 g, 10 min), 100 μl of genome extraction buffer was directly added to the pellet (100 nM Tris-HCl (pH 8.0), 5 mM EDTA, 0.2% SDS, 200 mM NaCl, and 100 μg/ml of proteinase K), and digestion was done overnight at 50 degrees Celsius. The next day, 250 μl of ethanol was added, and mixing was done by gently shaking up and down and inverting. The genome was recovered by centrifuge (1000 g, 10 min), washed with 70% ethanol, and air-dried. 100 μl of TE (10 mM Tris-HCl (pH 8.0), 1 mM EDTA) was added, and after letting stand for 30 minutes at 50 degrees C., this was dissolved at 4 degrees Celsius overnight.

(2) Analysis of Sequence Downstream of TRE

From the extracted genome, a sequence directly downstream of tetracycline inducible promoter was amplified by PCR (Perkin Elmer 9600) by TA cloning, and the sequence was analyzed.

Figure 5:
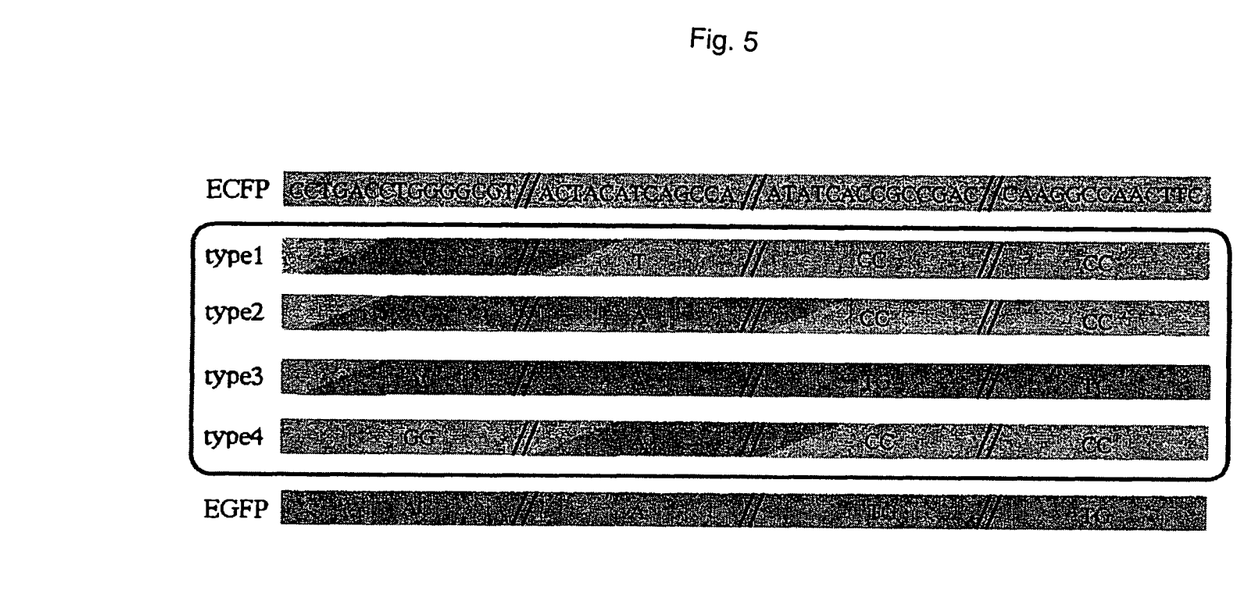
FIG. 5 shows analysis results of a novel genetic sequence. As a result of analysis of a sequence directly under TRE of a cell group with a strong fluorescent intensity, four novel types of recombinants, type1, type2, type3 and type4 were found. Further, ECFP and EGFP sequences are shown above and below the four types of sequences. Further, other than ECFP, only sequences differing for EGFP and ECFP are noted.

With 5 μl of genomic DNA fluid (corresponding to 5000 cells) as a template, 10 pmol respectively of upstream (5'-CCATAGAAGACACCGGGACCGATCC-3') (Sequence Number: 5) and downstream primer (5'-TG-CACGCTGCCGTCCTCGATGTTG-3') (Sequence Number: 6) was used. Using Pyrobest DNA Polymerase (manufactured by TaKaRa), a reaction was done at the 50 μl scale. The reaction conditions were, after 2 minutes at 98 degrees Celsius, 26 cycles were done of 30 seconds at 98 degrees Celsius, 30 seconds at 58 degrees Celsius, 1 minute at 72 degrees Celsius, and reaction was finally done for 5 minutes at 72 degrees Celsius. Subsequently, 1 μl of ExTaq DNA Polymerase (manufactured by TaKaRa) was added, and after reacting for 15 minutes at 72 degrees Celsius, the entire reaction fluid was separated by agarose gel electrophoresis. The bands corresponding to a light chain gene variable region were cut out, and after DNA was recovered by a Gel Extraction kit (manufactured by Qiagen), this was incorporated into a pCR2.1-TOPO vector, and transformed into *E. coli*. Plasmids were extracted, and sequenced using an ABI PRISM 377 DNA Sequencer (manufactured by Perkin Elmer). As a result, as shown in FIG. 5, it is clear that a chimera of ECFP and EGFP has been created. Among the four types of chimeras, 36 clones of type1, 1 clone of type2, 4 clones of type3, and 1 clone of type4 were respectively obtained. Additionally, 18 clones of ECFP were also obtained that are thought to be contaminants from sorting.

INDUSTRIAL APPLICABILITY

In the present invention, since objective genes having genetic diversity are formed spontaneously without the need for the production of a library, screening is possible immediately thereafter within an animal cell, so that it becomes possible to greatly reduce the amount of time until the objective gene is obtained.

Additionally, in the present invention, since homologous recombination is continuously induced in a variety of locations, it is in principle possible to increase the diversity of obtained recombinants, and this is applicable as an art that creates genes having novel activity and functions.

CITATIONS

Buerstedde, J. M. and Takeda, S. 1991. Cell 67:179-88

Chen, C. and Okayama, H. 1988. BioTechniques 6:632-638.

Crameri et al., 1998. Nature 391:288-291

DiSanto et al., 1995. Proc. Natl. Acad. Sci. USA 92:377-381

Elroy-Stein, O. and B. Moss. 1990. Proc. Natl. Acad. Sci. USA. 87:6743-6747.

Kaufman, R. J. 1990. Methods Enzymol. 185:487-511.

Neumann, E., M. et al., 1982. EMBO J. 1:841-845.

Rouet et al., 1994. Proc. Natl. Acad. Sci. USA 91:6064-6068

The invention claimed is:

1. A method of inducing homologous recombination between a gene and a DNA sequence comprising the step of promoting transcription of the gene by using a transcription promoter located 3' to the DNA sequence,
- wherein said recombination occurs at a genetic locus in a DT40 cell,
- wherein the gene is located 3' to the promoter,
- wherein the DNA sequence is similar to the gene for which homologous recombination is induced, and
- wherein the gene is exogenous.

2. The method of claim 1, wherein the gene is under additional transcription promotion by a cis-acting region comprising an enhancer or a nuclear matrix attachment region (MAR), or both.

3. The method of claim 1, wherein the DNA sequence is exogenous, further comprising the following steps prior to the step of promoting transcription:
   (a) ordering on a vector beginning with the 5' end, the DNA sequence, the transcription promoter 3' to the DNA sequence, and the gene 3' to the transcription promoter,
   (b) introducing the vector into the DT40 cell; and
   (c) incorporating the DNA sequence, the transcription promoter, and the gene into a chromosome.

4. The method of claim 3, wherein the vector further comprises an enhancer or a nuclear matrix attachment region (MAR), or both.

5. The method of claim 3, wherein the transcription promoter is an inducible promoter.

6. The method of claim 5, wherein the inducible promoter is a tetracycline inducible promoter.

7. The method of claim 3, wherein the gene is an enhanced cyan fluorescent protein (ECFP) gene.

8. The method of claim 3, wherein the DNA sequence is an enhanced green fluorescent protein (EGFP) genetic sequence.

9. The method of claim 2, wherein the enhancer is a chicken antibody light chain gene enhancer (3' enhancer), and the nuclear matrix attachment region (MAR) is chicken-derived.

10. The method of claim 1, wherein the transcription promoter is an inducible promoter.

11. The method of claim 10, wherein the inducible promoter is a tetracycline inducible promoter.

12. The method of claim 1, wherein the gene is an enhanced cyan fluorescent protein (ECFP) gene.

13. The method of claim 1, wherein the DNA sequence is an enhanced green fluorescent protein (EGFP) genetic sequence.

14. The method of claim 4, wherein the enhancer is a chicken antibody light chain gene enhancer (3' enhancer), and the nuclear matrix attachment region (MAR) is chicken-derived.

15. The method of claim 1, wherein the DNA sequence has 60% or greater sequence identity to the gene for which homologous recombination is induced.

* * * * *

SEQUENCE LISTING

<160> NUMBER OF SEQ ID NOS: 6

<210> SEQ ID NO 1
<211> LENGTH: 29
<212> TYPE: DNA
<213> ORGANISM: Gallus gallus
<220> FEATURE:
<221> NAME/KEY: primer_bind
<222> LOCATION: (8)..(29)
<223> OTHER INFORMATION:

<400> SEQUENCE: 1
gctgcagtgt ccttgggggt gaaattcag                              29

<210> SEQ ID NO 2
<211> LENGTH: 30
<212> TYPE: DNA
<213> ORGANISM: Gallus gallus
<220> FEATURE:
<221> NAME/KEY: primer_bind
<222> LOCATION: (9)..(30)
<223> OTHER INFORMATION:

<400> SEQUENCE: 2
gctctagaac tgcccccatt aaaaactttc                             30

<210> SEQ ID NO 3
<211> LENGTH: 30
<212> TYPE: DNA
<213> ORGANISM: Gallus gallus
<220> FEATURE:
<221> NAME/KEY: primer_bind
<222> LOCATION: (8)..(30)
<223> OTHER INFORMATION:

<400> SEQUENCE: 3
gctctagaag gcacagcgct gtcagggtgc                             30

<210> SEQ ID NO 4
<211> LENGTH: 30
<212> TYPE: DNA
<213> ORGANISM: Gallus gallus

<400> SEQUENCE: 4
ccgcggccgc gtggtgggag cgggcagggg                             30

<210> SEQ ID NO 5
<211> LENGTH: 25
<212> TYPE: DNA
<213> ORGANISM: Escherichia coli
<220> FEATURE:
<221> NAME/KEY: primer_bind
<222> LOCATION: (1)..(25)
<223> OTHER INFORMATION:

<400> SEQUENCE: 5
ccatagaaga caccgggacc gatcc                                  25

<210> SEQ ID NO 6
<211> LENGTH: 24
<212> TYPE: DNA
<213> ORGANISM: Escherichia coli
<220> FEATURE:
<221> NAME/KEY: primer_bind
<222> LOCATION: (1)..(24)
<223> OTHER INFORMATION:

```
<400> SEQUENCE: 6
tgcacgctgc cgtcctcgat gttg                                                  24
```